United States Patent [19]

Littmann

[11] 3,951,230

[45] Apr. 20, 1976

[54] MULTI-SOUND CHAMBER STETHOSCOPE

[75] Inventor: David Littmann, Needham Township, Norfolk County, Mass.

[73] Assignee: Minnesota Mining and Manufacturing Company, St. Paul, Minn.

[22] Filed: Jan. 31, 1975

[21] Appl. No.: 545,827

Related U.S. Application Data

[63] Continuation-in-part of Ser. No. 511,516, Oct. 3, 1974, abandoned.

[52] U.S. Cl............................... 181/131; 181/137
[51] Int. Cl.²........................................ A61B 7/02
[58] Field of Search........................... 181/131, 137

[56] References Cited
UNITED STATES PATENTS

| | | | |
|---|---|---|---|
| 2,258,743 | 10/1941 | Dax.................................. | 181/131 |
| 3,152,659 | 10/1964 | Littmann........................... | 181/137 |
| 3,157,246 | 11/1964 | Howell.............................. | 181/137 |
| 3,224,526 | 12/1965 | Weber............................... | 181/137 |
| 3,472,335 | 10/1969 | Allen................................. | 181/137 |
| 3,515,239 | 6/1970 | Machlup et al.................... | 181/137 |
| 3,630,308 | 12/1971 | Ravin............................... | 181/131 |
| 3,712,409 | 1/1973 | Kizakisz et al.................... | 181/137 |
| 3,767,003 | 10/1973 | Shacklock......................... | 181/137 |

FOREIGN PATENTS OR APPLICATIONS

| | | | |
|---|---|---|---|
| 821,374 | 8/1937 | France.............................. | 181/131 |

Primary Examiner—Stephen J. Tomsky
Attorney, Agent, or Firm—Alexander, Sell, Steldt & DeLaHunt

[57] ABSTRACT

A stethoscope having a head wherein a diaphragm sound chamber is disposed within a housing which allows for the head to be used as a diaphragm sound chamber or a bell sound chamber without removal of the stethoscope head from the patient.

7 Claims, 8 Drawing Figures

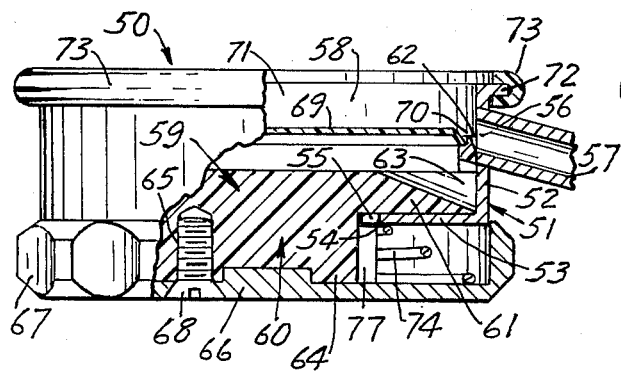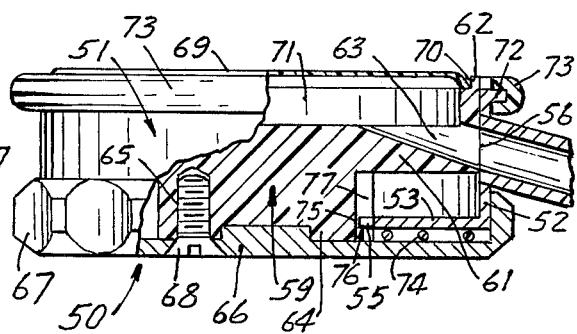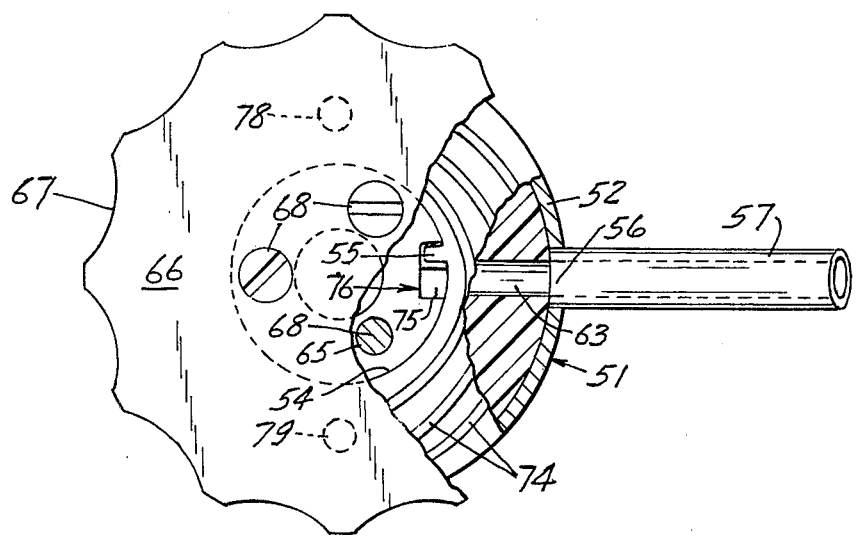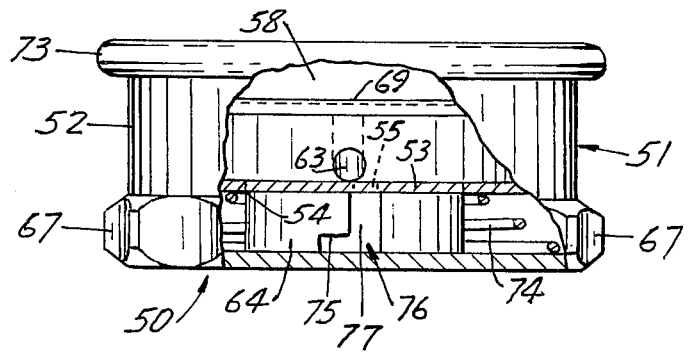

MULTI-SOUND CHAMBER STETHOSCOPE

This is a continuation-in-part of U.S. application Ser. No. 511,516 filed Oct. 3, 1974 now abandoned.

This invention relates to multi-sound chamber stethoscopes. Particularly, this invention relates to stethoscopes wherein one sound chamber is movable in the other.

Two types of stethoscope sound chambers are commonly available, the open or bell type and the diaphragm type. The open or bell type is best suited to listening to the low pitched heart sounds such as presystolic and some systolic murmurs, mitral diastolic murmurs, first, second, third and fourth heart sounds and gallop rhythms. Diaphragm sound chambers allow one to hear higher frequency sounds.

Since, for complete diagnosis, it is necessary to use both the bell and the diaphragm sound chambers, stethoscopes with both attached have been developed as illustrated by those disclosed in U.S. Pat. Nos. 3,224,526, 3,630,308 and 3,515,239. These stethoscopes all involve designs whereby the chest piece is moved from the body of the patient in order to change from the bell to the diaphragm sound chamber and vise versa. It is important to the doctor that the impression from the previously heard heartbeat still be present in his mind when he hears the next beat. Thus, rapid, agile switching from the bell to the diaphragm is required in order to minimize the risks that a significant number of heartbeats will be missed. Such rapid switching generally involves a relocation of the sound chamber on the patient. A stethoscope had been sought which would facilitate the rapidity of the change from the bell to diaphragm sound chamber and which will allow switching without removal from the patient.

Such a stethoscope has been found. It has a head comprising a housing having a tubular portion with a central opening, a first end defining a rim adapted for contacting a patient, and an aperture through said housing to said central opening and spaced a predetermined distance from said rim for transmission of sound from said central opening; and a diaphragm sound chamber disposed within said central opening comprising a rigid wall member with a periphery in sliding engagement within said central opening and defining a cavity opening towards said rim, and a diaphragm on said wall member to cover said cavity opening, said wall member having an aperture therethrough to said cavity for transmission of sound from said cavity spaced from said diaphragm a distance approximately equal to said predetermined distance, said diaphragm sound chamber being slidable between a first position with said apertures in alignment and said diaphragm at said rim and a second position within said housing with said diaphragm spaced from said rim to afford communication between the aperture in said housing and the space between said rim and said diaphragm;

whereby said head may be used as a diaphragm sound chamber by positioning said diaphragm sound chamber at said first position and may be used as a bell sound chamber by positioning said diaphragm sound chamber at said second position.

The invention will be described in more detail with reference to the following drawings in which FIG. 1 is a bottom view of one embodiment of a stethoscope containing one embodiment of the stethoscope head of the present invention;

FIG. 5 is a side view with portions in section of another embodiment of the stethoscope head of the present invention in one position;

FIG. 6 is a side view with portions in section of the embodiment of the stethoscope head of the present invention shown in FIG. 5 except that the head is in the other position;

FIG. 7 is a top view with portions in section of the embodiment of the stethoscope head of the present invention shown in FIGS. 5 and 6;

FIG. 8 is another side view with portions broken away of the embodiment of the stethoscope head of the present invention depicted in FIGS. 5, 6 and 7.

Figure 1:
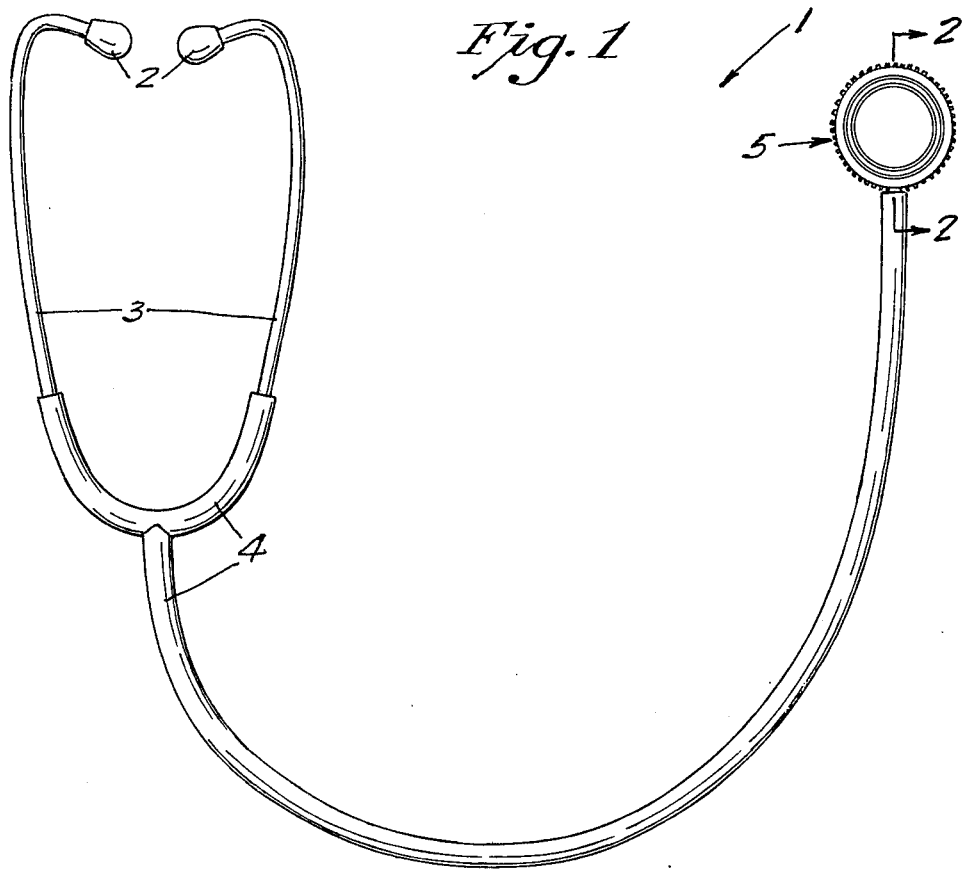

The stethoscope which is shown in FIG. 1 contains ear tips 2 attached to ear tubes 3. The ear tubes 3 are attached to connecting tube 4 which is in turn attached to stethoscope head 5. Stethoscope head 5 is shown in detail in FIGS. 2 and 3.

Stethoscope head 5 comprises housing 6 comprising tubular portion 7 containing central opening 8, aperture 9 containing pipe 10 which is attached to tube 4, ring 11 and wall 12 containing threaded aperture 13. Disposed within central opening 8 of housing 6 is diaphragm sound chamber 14 comprising rigid wall member 15 comprising periphery 16 containing aperture 25, rear wall 17, cylindrical protrusion 18 containing threads 19, which protrusion is attached to disc 20 having knurled cylindrical periphery 21. The rigid wall member 15 forms cavity 22 which is covered by diaphragm 23.

Figure 2:
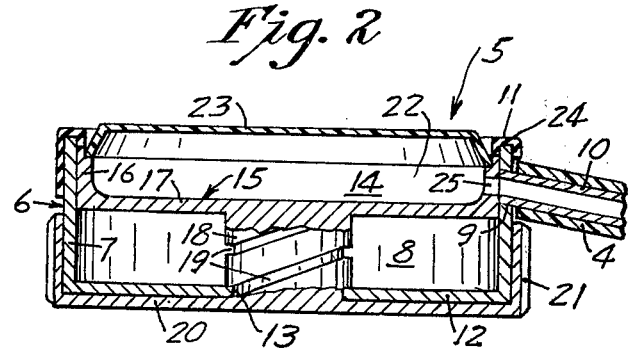
FIG. 2 is a section view taken along line 2—2 of one embodiment of the stethoscope head of the present invention depicting one position in said head.

In FIG. 2 the stethoscope head 5 is shown in a first position where the diaphragm sound chamber 14 is in position for use, that is, the diaphragm 23 of diaphragm sound chamber 14 is at the rim 24 of housing 6. Aperture 25 of diaphragm sound chamber 14 in this position is in alignment with aperture 9 in housing 6. In this position the diaphragm 23 can extend beyond the rim 24 of housing 6 or can be coplanar with it or slightly recessed within it. The diaphragm 23 must be in a position so that it can be contacted with the patient and the aperture 25 of the diaphragm sound chamber 14 must be in at least partial alignment with aperture 9 of housing 6 so that the sound from the diaphragm sound chamber 14 can be transmitted from cavity 22 through apertures 25 and 9, pipe 10 and tube 4 to the ears of the doctor. Disc 20 is sealed against wall 12 in this position.

Figure 3:
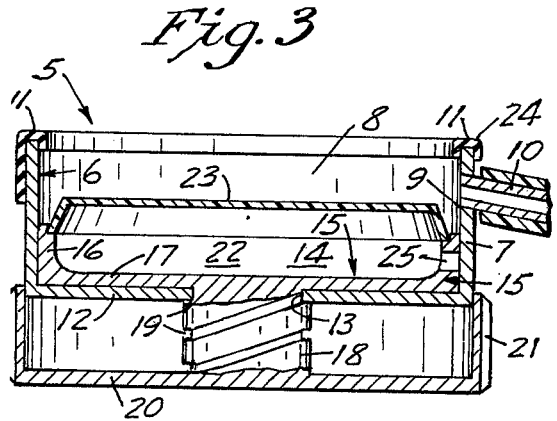
FIG. 3 is a section view taken along line 2—2 of one embodiment of the stethoscope head of the present invention depicting the other position in said head.

In FIG. 3 the cylindrical knurled periphery 21 of disc 20 has been rotated so that threads 19 which cooperate which threaded aperture 13 of housing 6 cause the diaphragm sound chamber 14 to be moved to the second position where rear wall 17 of diaphragm sound chamber 14 is in contact with wall 12 of housing 6. In this position diaphragm 23 is no longer at the rim 24 of the housing 6 but is sufficiently recessed within the central opening 8 of housing 6 that the aperture 9 is at least partially uncovered and aperture 25 of diaphragm sound chamber 14 is no longer in alignment with aperture 9 of housing 6. In this position the tubular portion 7, diaphragm 23, wall 12, rear wall 17 and diaphragm sound chamber periphery 16 form a bell sound chamber.

In use, stethoscope head 5 is placed on a patient by the doctor in either of the first or second positions. The heart is listened to in one position, for instance, the first position where higher frequency sounds can be heard and the diaphragm 23 is at the rim 24 of the housing 6. If it is desired to listen to the lower frequency sounds, the knurled cylindrical periphery 21 attached to disc 20 is rotated to cause the diaphragm sound chamber 14 to be recessed to the position shown in FIG. 3. This is done without removing the stethoscope head 5 from the body of the patient. In this position the stethoscope head 5 acts as a bell sound chamber. Thus, the lower pitched sounds would be more audible. In this position the ring, normally of a material with low thermal diffusivity such as plastic or rubber, 11 acts to form a seal between the skin of the patient and the stethoscope head 5. A substantially airtight chamber is formed between the skin, ring 11, tubular portion 7, wall 12, rear wall 17, diaphragm sound chamber periphery 16 and diaphragm 23. Sounds are transmitted from this airtight chamber through aperture 9, pipe 10 and tube 4 to the doctor.

Figure 4:
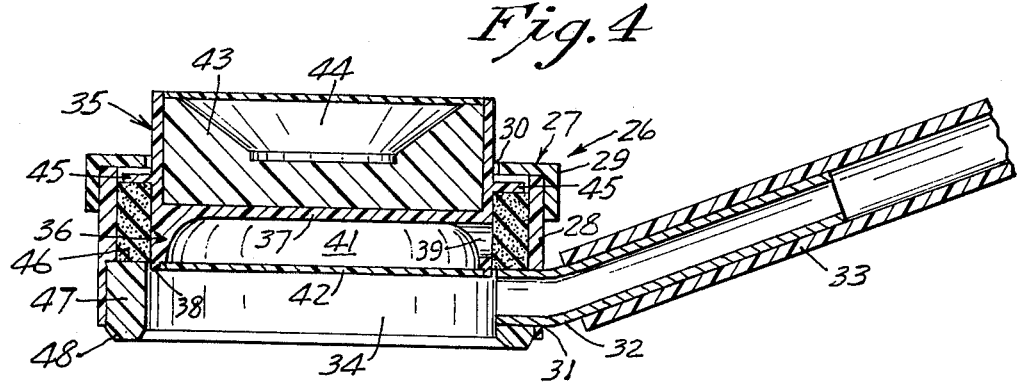
FIG. 4 is a section view of another embodiment of the stethoscope head of the present invention.

FIG. 4 depicts a section of another embodiment of the stethoscope head of the invention. This stethoscope head 26 comprises housing 27 having tubular portion 28 with cap 29 attached thereto containing aperture 30. Housing 27 also contains aperture 31 for transmission of sound from the stethoscope head 26 through pipe 32 which is connected to tube 33 which leads to the ear tubes (not shown) of the stethoscope. Central opening 34 has disposed therein diaphragm sound chamber 35 which comprises rigid wall member 36 containing rear wall 37 and periphery 38 containing aperture 39. Rigid wall member 36 defines a cavity 41 which is covered by diaphragm 42. Attached to rear wall 37 is button 43 containing finger recess 44. Button 43 has projection 45 attached thereto. Projection 45 cooperates with biasing resilient material 46 and ring 47 having rim 48 to hold diaphragm sound chamber 35 in position.

As depicted in FIG. 4, the stethoscope head 26 is in the bell sound chamber position, i.e., the second position. That is, the diaphragm sound chamber 35 is biased by biasing material 46 away from rim 48. In this position aperture 39 is not in alignment with aperture 31 and pipe 32. In order to place the stethoscope head 26 in the position wherein diaphragm sound chamber 35 is in position for use, button 43 is pressed and resilient biasing material is compressed by projection 45. Diaphragm sound chamber 35 is moved so that diaphragm 42 is at rim 48 and aperture 39 is at least in partial alignment with aperture 31 and pipe 32. In this position the stethoscope head 26 acts as a diaphragm sound chamber, this being the first position whereas in the outer position previously described and depicted in FIG. 4 the stethoscope head 26 acts as a bell sound chamber. In both positions the biasing material forms a sound tight seal to prevent the loss of sound under consideration and to prevent the entrance of extreme outside sounds.

FIGS. 5–8 depict another embodiment of the stethoscope head of the present invention. This stethoscope head 50 comprises housing 51 having tubular portion 52, top wall 53, hole 54 and projection 55 extending therein. Housing 51 also contains aperture 56 for transmission of sound from stethoscope head 50 through pipe 57 which is connected to a tube leading to ear tubes (both not shown) of the stethoscope. The central opening 58 of housing 51 has disposed therein diaphragm sound chamber 59 comprising wall member 60 containing rear wall 61 and periphery 62 containing aperture 63. Wall member 60 also contains cylindrical projection 64 which contains screw holes 65 for attaching the diaphragm sound chamber 59 to disc member 66 which has attached to it knurled periphery 67. Attachment is by means of screws 68. Diaphragm sound chamber 59 contains diaphragm 69 which is attached to the edge 70 of the cavity 71 which is defined by rear wall 61 and cylindrical periphery 62. Housing 51 has rim 72 which is covered by ring 73.

FIG. 5 depicts the stethoscope head in the mode wherein the diaphragm sound chamber 59 is away from rim 72 and aperture 56 is uncovered. In this position the stethoscope head is a bell sound chamber. The stethoscope head is retained in this position by spring 74 which resiliently maintains the diaphragm sound chamber 59 by force applied to rear wall 61 and disc member 66.

In FIG. 6 the stethoscope head is shown in the diaphragm sound chamber position. In this case the diaphragm 69 is at rim 72 and aperture 63 of diaphragm sound chamber 59 is in line with aperture 56 in housing 51. The stethoscope head is placed in this position by application of force on disc member 66 and knurled periphery 67 which causes spring 73 to compress and diaphragm sound chamber 59 to be pushed to a position where the diaphragm 69 is at rim 72. A twist of knurled periphery 67 clockwise causes projection 55 to move into slot 75 of locking means 76 comprising slot 75 and vertical channel 77. The locking means 76 excluding projection 55 is formed in the cylindrical projection 64 of diaphragm sound chamber 59.

FIG. 7 is a top view of the embodiment of the stethoscope head shown in FIGS. 5 and 6. In this view screws 68 are all shown. The projection 55 is in slot 75, therefore, the stethoscope is in the diaphragm sound chamber position with diaphragm sound chamber aperture 63 in line with aperture 56 of of housing 51. This view also shows holes 78 and 79 in top wall 53. Holes 78 and 79 are present to allow for air passage when the stethoscope head is changed from the bell sound chamber position to the diaphragm sound chamber position.

FIG. 8 depicts the stethoscope head in the bell sound chamber position and shows more clearly projection 55 and the locking means 76 containing projection 55 in channel 77. When the projection 55 is moved from the position shown in FIG. 8 through the entire length of channel 77 and knurled periphery 67 is twisted clockwise, projection 55 is in slot 75 and the stethoscope is locked in the diaphragm sound chamber position.

The resilient material 46 of the embodiment shown in FIG. 4 can be materials such as resilient foam, rubber, springs or the like. In the embodiments depicted, the stethoscope heads are made of materials normally utilized in stethoscopes such as plastic or metal and can be made by well known techniques such as stamping, molding, gluing, press fitting, etc. Stainless steel is a preferred material of construction. The diaphragm of the stethoscope is normally fiberglass reinforced plastic or a similar material.

What is claimed is:

1. A stethoscope head comprising a housing having a tubular portion with a central opening, a first end defining a rim adapted for contacting a patient, and an aperture through said housing to said central opening and spaced a predetermined distance from said rim for transmission of sound from said central opening; and a diaphragm sound chamber disposed within said central opening comprising a rigid wall member with a periphery in sliding engagement within said central opening and defining a cavity opening towards said rim, and a diaphragm on said wall member to cover said cavity opening, said wall member having an aperture therethrough to said cavity for transmission of sound from said cavity spaced from said diaphragm a distance approximately equal to said predetermined distance, said diaphragm sound chamber being slidable between a first position with said apertures in alignment and said diaphragm at said rim and a second position within said housing with said diaphragm spaced from said rim to afford communication between the aperture in said housing and the space between said rim and said diaphragm;

whereby said head may be used as a diaphragm sound chamber by positioning said diaphragm sound chamber at said first position and may be used as a bell sound chamber by positioning said diaphragm sound chamber at said second position.

2. A stethoscope head according to claim 1, wherein said head further includes means coupled between said housing and said rigid wall member and adapted for manual activation to move said diaphragm sound chamber between said first and second positions.

3. A stethoscope head according to claim 1, wherein said central opening and the periphery of said rigid wall member are cylindrical, and said housing and said rigid wall member are formed with cooperating screw threads for supporting said diaphragm sound chamber within said housing, and an end of said rigid wall member opposite said diaphragm projects from an end of said housing opposite the rim and is adapted for manual engagement to rotate said diaphragm sound chamber between said first and second positions.

4. A stethoscope head according to claim 1 further comprising:

means coupled between said housing and said diaphragm sound chamber limiting movement therebetween to movement between said first and second positions;

means for biasing said diaphragm sound chamber toward said second position; and an end on said rigid wall member opposite said diaphragm adapted for manual engagement adjacent an end of said tubular portion opposite said rim to press said diaphragm sound chamber to said first position in opposition to said biasing means.

5. A stethoscope head according to claim 4 further comprising means coupled between said rigid wall member and said housing for locking said diaphragm sound chamber in said first position after said diaphragm sound chamber is moved to said first position in opposition to said biasing means.

6. A stethoscope head comprising a housing having a tubular portion with a cylindrical central opening, a first end defining a rim adapted for contacting a patient, an aperture through said housing to said central opening and spaced a predetermined distance from said rim for transmission of sound from said central opening, and screw threads formed in said housing;

a diaphragm sound chamber disposed within said central opening comprising a rigid wall member with a cylindrical periphery and defining a cavity opening towards said rim, and a diaphragm on said wall member to cover said cavity opening, said rigid wall member having an aperture therethrough to said cavity for transmission of sound from said cavity spaced from said diaphragm a distance approximately equal to said predetermined distance, screw threads in said housing, and an end of said rigid wall member opposite said cavity projecting from an end of the housing opposite the rim and adapted for manual engagement to slide said diaphragm sound chamber along the screw threads in said housing between a first position with said apertures in alignment and a second position within said housing with said diaphragm positioned proximate said aperture through said housing;

whereby said head may be used as a diaphragm sound chamber by positioning said diaphragm sound chamber at said first position, and may be used as a bell sound chamber by positioning said diaphragm sound chamber at said second position to afford communication between the aperture in said housing and the space between said rim and said diaphragm.

7. A stethoscope comprising means for conveying a sound from a stethoscope head and the stethoscope head of claim 1 attached to said means.

* * * * *